United States Patent [19]

Schmidt

[11] Patent Number: 4,600,008
[45] Date of Patent: Jul. 15, 1986

[54] INSTRUMENT FOR REMOVING FOREIGN SUBSTANCES FROM THE EYE

[76] Inventor: Richard G. Schmidt, Rte. #1, Box 259, Jackson, Mo. 63755

[21] Appl. No.: 569,467

[22] Filed: Jan. 9, 1984

[51] Int. Cl.⁴ ............................................. A61B 17/50
[52] U.S. Cl. .................................... 128/357; 128/304; 128/756
[58] Field of Search ................ 128/1.4, 304, 320, 326, 128/357, 756, 757, 759

[56] References Cited

U.S. PATENT DOCUMENTS

| | | | |
|---|---|---|---|
| 1,597,500 | 8/1926 | Alexander et al. | 128/357 X |
| 2,555,550 | 6/1951 | Krivaner et al. | 128/357 |
| 2,856,933 | 10/1958 | Hildebrand et al. | 128/326 X |
| 3,476,114 | 11/1969 | Shannon et al. | 128/326 |
| 3,665,926 | 5/1972 | Flores | 128/326 |
| 3,786,816 | 1/1974 | Wolvek | 128/326 X |

FOREIGN PATENT DOCUMENTS 1224482  2/1960  France ................. 128/304

Primary Examiner—Dalton L. Truluck
Attorney, Agent, or Firm—Haverstock, Garrett & Roberts

[57] ABSTRACT

An instrument for manipulating on the surface of the eye to remove foreign substances therefrom comprising an elongated body member having spaced opposed ends and being of a length to facilitate the holding and manipulation thereof, a flexible thread-like member extending from at least one end of the elongated body member to form a loop for engaging and manipulating on the surface of the eye, the size of the loop being adjustable to enclose different areas of the eye.

9 Claims, 10 Drawing Figures

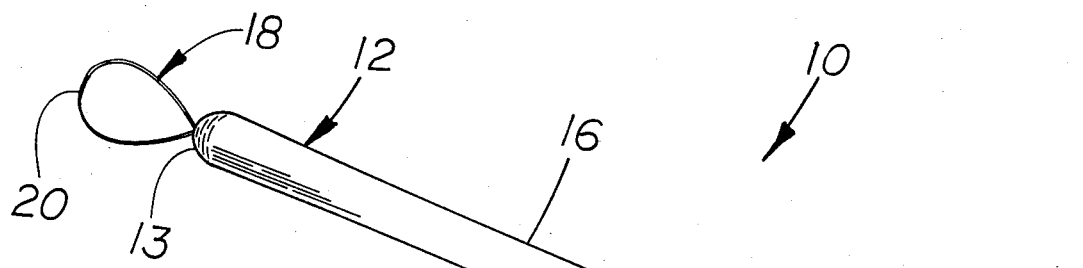
FIG. 1
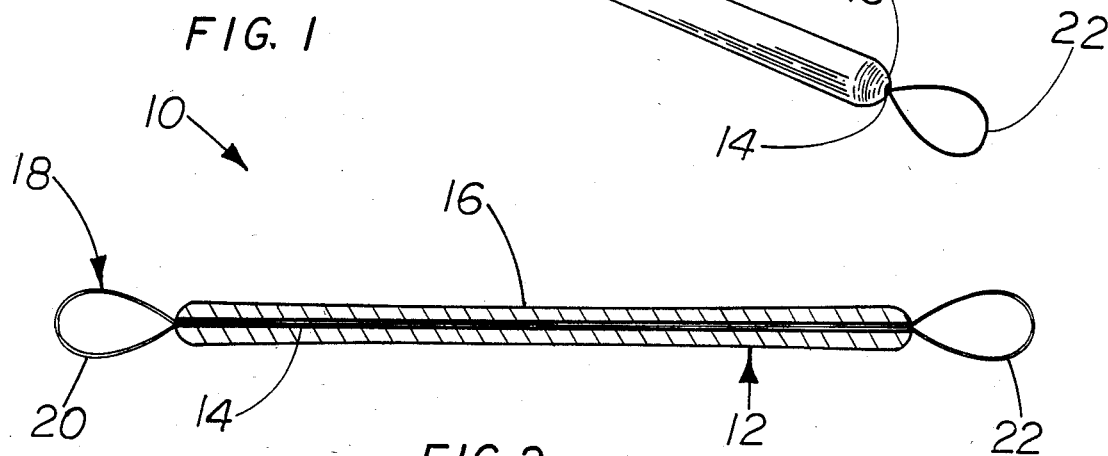
FIG. 2
FIG. 5
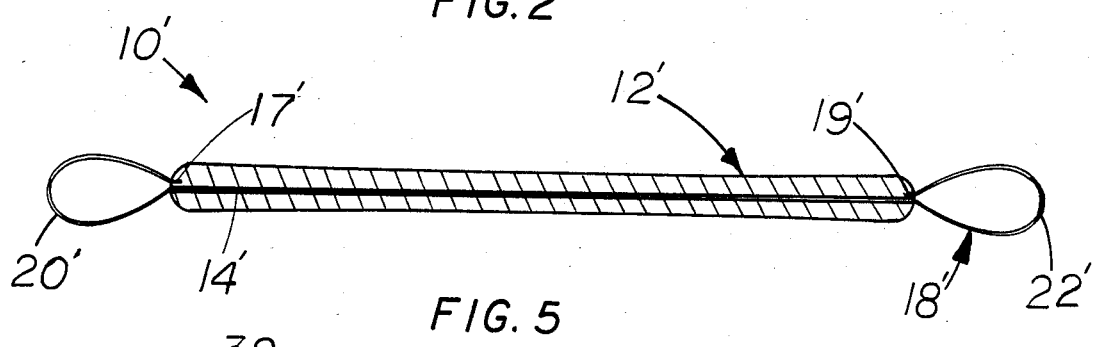
FIG. 6
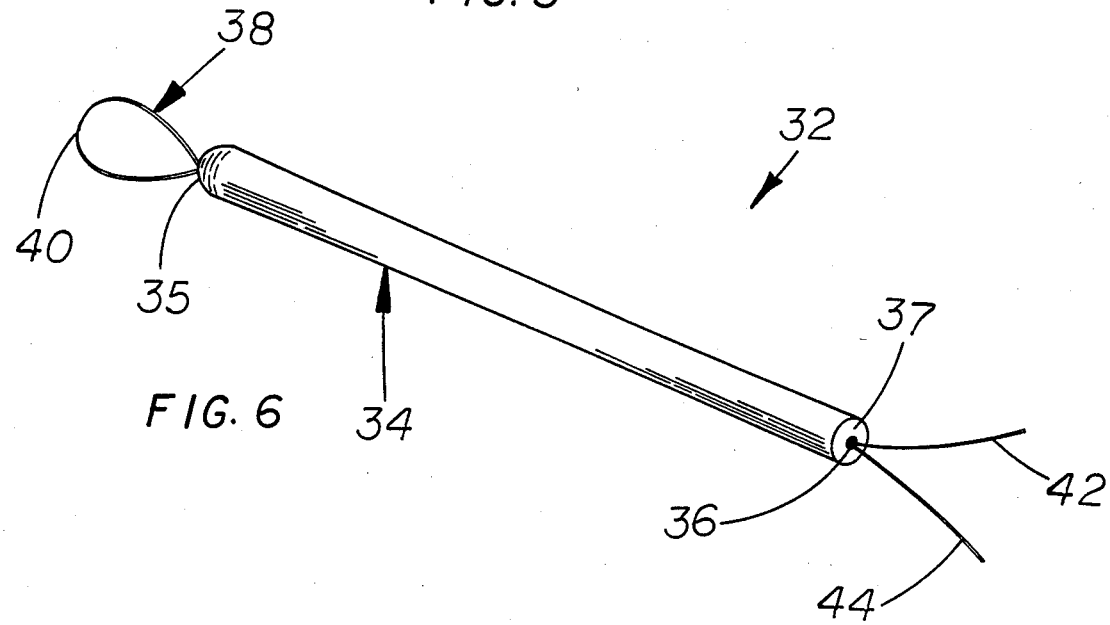

INSTRUMENT FOR REMOVING FOREIGN SUBSTANCES FROM THE EYE

The present invention relates to several embodiments of a relatively simple instrument for removing foreign substances from the surface of the eye and, more particularly, to an instrument having at least a portion of a relatively thin, sterile, flexible thread-like member extending from at least one end thereof, the flexible thread-like member being shaped in the form of a loop and being adaptable for being placed on the surface of the eye between the eyeball and the underside portion of the eyelid. The loop portion of the thread-like member is adjustable to accommodate different areas of the eye surface and the present instrument is used mainly to remove foreign substances located on both the surface of the eye and the underside portion of the eyelid.

The human eye is a complex organism which is susceptible to a score of disorders and diseases and, most particularly, is easily susceptible to irritation caused by the collection of foreign debris such as sand, dust, and other foreign bodies which gather on and/or around the surface of the eye and under the eyelid. Once a foreign body is introduced into the eye, if it is allowed to remain within the eye for a period of time, inflammation may quickly result and this may further result in trauma, discomfort, infection, and/or other damage to the eye. Any of these conditions may result in temporary and/or permanent impairment of vision.

Many different eye cleansing means are known and have been employed for use in removing foreign substances from the eye. Most of these known means involve the use of a washing solution for holding and washing the eye and flushing foreign debris therefrom. These known eye cleansing means usually require the use of an eye cup or other similar device for irrigating the eye with the wash solution. Such known means, for the most part, are generally awkward and cumbersome to carry on one's person and therefore are normally not available to the user to provide immediate, on the spot, relief whenever a foreign substance enters the eye. In addition, a wide variety of eye drop solutions are also available for providing relief from minor eye irritation due to dust, smoke, smog, plant allergies and other common eye irritating agents but such eye drop solutions are not particularly effective for removing foreign substances from the eye.

The closest known prior art to the present instrument is an eye magnet device advertised in the Fall 1983 Conney First Aid And Personal Safety Supplies Catalog. This device includes a handle member, a first member engageable with one end portion of the handle member having a stainless steel magnet associated therewith for removing magnetized foreign bodies such as metal particles from the eye, and a second member engageable with the opposite end portion of the handle member having a small substantially rigid nylon loop associated therewith for removing non-magnetized foreign bodies from the eye. The nylon loop portion of this device is fixedly secured to a substantially sharp end portion of the second member, the insertion of which into the eye could be dangerous and could scratch or otherwise cause damage to the eye. The eye magnet portion of this device also requires the insertion of a rather sharp magnetized instrument into or adjacent to the eye in order to effect removal of metal particles and this could even more likely cause injury to the eye during use. The known device, however, provides no means whatsoever for adjusting the size of the loop portion to be placed against the eyeball and it provides no means whatsoever for maintaining the sterility of the nylon loop prior to use. This is not true of the present instrument as will be hereinafter explained. In addition, the known device is primarily for use with the eyelid in an open position while the present instrument can be used when the eyelid is open or closed. It is therefore desirable to provide a relatively simple, safe and sanitary means for effectively removing foreign substances from the eye, which means can be fully adjustable as necessary and can be relatively easily and safely manipulated to effect relief.

The various embodiments of the present instrument diclosed herein overcome many of the disadvantages and shortcomings associated with the known means for removing debris from the eye, and teach the construction and operation of a relatively simple and inexpensive instrument for easily, quickly and safely removing irritating substances from the eye. One embodiment of the present instrument comprises an elongated body member having first and second opposite end portions and a passageway extending therethrough. A flexible thread-like member of suitable length is positioned in the passageway and extends therein and therethrough in such a manner that a portion of the thread-like member extends in loop fashion from both opposite ends thereof. The thread-like member is preferably made from a relatively thin, flexible and sterile material such as a fine gauge surgical suturing material having surface characteristics coarse enough to engage foreign substances located on the eye surface when moved thereacross yet smooth enough so as not to scratch or otherwise damage the eye surface. This is especially important since the eye surface is formed of a sensitive, complex, transparent tissue which is the primary refracting surface necessary for proper image formation and such tissue can be easily scarred and damaged. The elongated body member or holder is preferably made of a durable material such as a lightweight relatively rigid plastic material able to withstand moderate impact and normal usage, and it may include means to facilitate the gripping thereof.

The passageway extending through the body member is dimensioned so as to relatively tightly engage the reaches of the thread-like member extending therethrough. This engagement is such that the size of the loop portion of the thread-like member extending from one or both opposite ends of the body member are steadfastly maintained while, at the same time, also allowing some movement of the thread-like member within the passageway so that the size of each loop portion may be adjusted by simply pulling the thread-like member at one end in the desired direction. This allows a user to easily adjust the size of the loop portion to be placed against the eyeball, preferably without physically touching that portion of the thread-like member which will be against the eye. This maintains and preserves the sterility of that portion of the thread-like member. Once a loop portion of the thread-like member is adjusted as aforesaid, the user simply manipulates the elongated body member with one hand to position the loop portion of the thread-like member against the eye surface while the other hand is free to raise the eyelid of the affected eye. Once the loop is properly positioned, the eyelid can be reclosed and if necessary slight pressure can be applied thereagainst, and the loop portion of the thread-like member is then pulled across the surface of the eye in a single, smooth and steady motion. Movement of the thread-like member across the eye surface engages any foreign debris located thereon within the confines of the loop portion thereof and removes such debris from both the eye surface and the underside portion of the eyelid. The loop portion of the thread-like member should be adjustable to a size which will enable a user to manipulate the loop portion across any portion of the eyeball including across substantially the entire frontal eyeball surface in a single process.

Various other embodiments of the present invention include other means including means for adjusting the loop end portion of the thread-like member prior to use. Although it is anticipated that the present instruments will be made so as to be disposable after use, they can also be constructed for repeated use, if desired. It is also anticipated that each of the present instruments will be individually packaged in a sanitary wrapping so that they can be easily carried and stored for use wherever and whenever desired.

It is therefore a principal object of the present invention to provide an inexpensive, safe and efficient means for removing foreign substances from the eye.

Another object is to provide a safe and sanitary means for simultaneously removing foreign substances from both the surface of the eye and the underside portion of the eyelid in a single operation.

Another object is to provide means for removing foreign substances from the eye which can be operated by persons of widely varying ages and abilities.

Another object is to provide an instrument for removing foreign bodies from the eye which can be made so as to be disposable or constructed for repeated use.

Another object is to provide an instrument for removing foreign bodies from the eye which is relatively simple structurally and operationally, is compact, and can be packaged in a sanitary condition.

Another object is to provide an instrument for removing foreign bodies from the eye which is adjustable to cover different areas of the eye surface.

Another object is to provide an instrument for removing foreign substances from the eye which utilizes a flexible thread-like eyeball engaging member that is coarse enough to engage and remove foreign bodies located on the eye surface when moved thereacross yet smooth enough so as not to scratch or otherwise scar or damage the eye surface.

Another object is to provide an instrument for removing foreign substances from the eye which can be easily adjusted to accommodate different areas of the eye surface.

These and other objects and advantages of the present invention will become apparent to those skilled in the art after considering the following detailed specification in conjunction with the accompanying drawings, wherein:

FIG. 1 is a perspective view showing one embodiment of an instrument for removing foreign substances from the eye constructed according to the teachings of the present invention;

FIG. 2 is an enlarged cross-sectional view through the center of the instrument of FIG. 1 showing use of the instrument with an endless thread-like member;

FIG. 5 is an enlarged cross-sectional view similar to FIG. 2 showing use of a non-continuous thread-like member;

FIG. 6 is a perspective view showing another embodiment of the present instrument;

Figure 3:
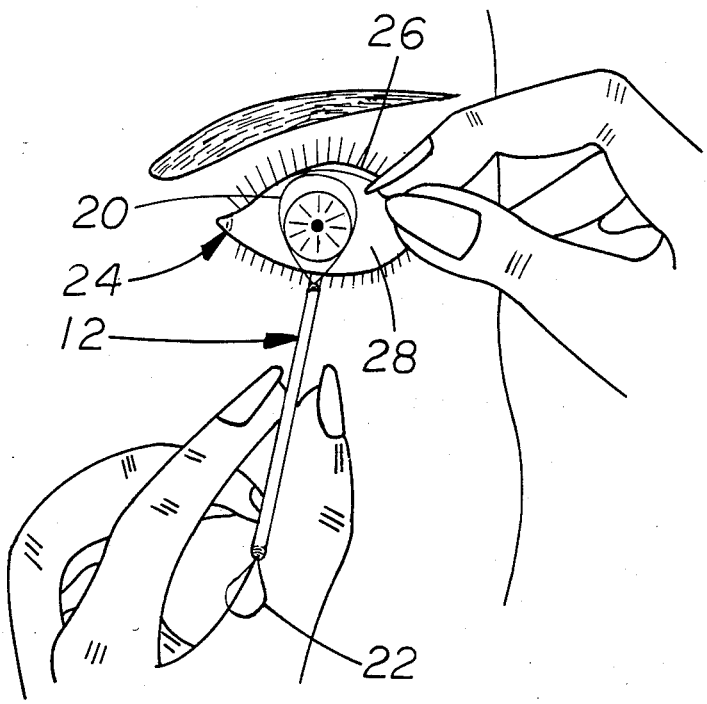
FIGS. 3 and 4 are views illustrating the operation and use of the instrument of FIGS. 1 and 2.

Referring to the drawings more particularly by reference numbers wherein like numerals refer to like parts, number 10 in FIGS. 1 and 2 identifies one embodiment of an instrument for manipulating on the surface of an eyeball to remove foreign substances therefrom constructed according to the teachings of the present invention. The instrument 10 includes an elongated body member 12, preferably tubular in shape, having an open ended passageway 14 extending therethrough. The body member 12 is dimensioned lengthwise such that it can be easily and comfortably held in a user's hand for manipulation and the outer surface thereof may be serrated or otherwise scored so as to facilitate the gripping thereof. The end portions or surfaces 13 and 15 of the member 12 are preferably made smooth and are rounded since these portions will be positioned adjacent the surface of the eye when the device 10 is used. This reduces the possibility for damaging the eye by the end portion of the member 12. The side portions of the body member 12 may also be slightly concaved as at 16 to further facilitate holding the instrument.

A continuous flexible thread-like member 18 of suitable length is positioned in the passageway 14 and extends therethrough and from both opposite ends of the body member 12 as shown in FIG. 2. The ends of the thread-like member 18 extending from the opposite ends of the member 12 are identified as end portions 20 and 22 and each portion 20 and 22 is formed into a loop of the same or of different sizes. The thread-like member 18 is preferably made from a relatively thin, flexible material such as from a fine gauge surgical suturing material having a flexural rigidity sufficient to maintain the portions 20 and 22 in looped fashion extending from both opposite ends of the member 12. The material comprising the member 18 should be coarse enough to engage foreign bodies such as particles of dirt or sand on the eye surface when moved thereacross yet sufficiently smooth so as not to scratch, scar or otherwise damage the eye surface. This is important because the loop portions 20 and 22 of the thread-like member 18 are the portions that will be placed against and moved across the surface of the eye when removing foreign debris therefrom. It is also important that the material selected for the member 18 be soft and flexible enough to conform to the shape of the eye when inserted between the eye surface and the eyelid and that said material be sanitary and non-toxic so as not to cause inflammation and/or infection of the eye in which it comes in contact. Although it is generally preferred that the member 18 be made from certain gauges of extremely fine, sterile suturing material, it is also recognized that other suitable materials such as certain nylon and polyproplyene type materials, horse hair and human hair can be sterilized and used.

The present instrument 10 is also constructed such that the size of the loop portions 20 and 22 may be adjusted to different sizes. This adjustability is accomplished by specifically dimensioning the passageway 14 such that the body member 12 frictionally engages the reaches of the thread-like member 18 extending therethrough in such a way that some movement of the member 18 within body member 12 can be made as desired. This enables the size of each loop portion 20 and 22 to be adjusted by merely manipulating the opposite end portion of the thread-like member 18 in the desired direction. For example, if the loop portion 20 needs to be reduced in size, one merely grasps the loop portion 22 and pulls one or both of the reaches to draw the thread-like member 18 through the body 12. In contrast, if the loop portion 20 needs to be enlarged in size, one pushes on the loop portion 22 if the material is stiff enough. This enlarging of the loop 20 may also be accomplished by pulling on the loop portion 20 in which case a sterile member (not shown) should be placed in the loop 20 to pull it out. This enables a user to precisely adjust the size of the loop thread-like portion to be placed against the eyeball and in most cases this can be done without physically touching the loop portion that is to be used against the eye thereby maintaining and preserving sterility. Maintaining the sterility of that portion of the thread-like member which is to engage the surface of the eye prior to use is extremely important since this will minimize the possibility for irritation and/or infection resulting from use of the subject instrument. The adjustability of the loop portions 20 and 22 should also be such that their size can be enlarged sufficiently so as to enable a user to manipulate the loop portions 20 and/or 22 across any portion of the eye surface including across substantially the entire frontal eye surface, if so desired, in a single process.

It is also anticipated that the instrument 10 will be packaged in a sterile wrapping preferably with one loop portion of the thread-like member 18 being initially packaged sufficiently larger than the other so that only the smaller loop portion generally need be manipulated to adjust the loop size of the larger loop portion. Once the desired size of the loop portion of the thread-like member to be positioned adjacent the eye surface is achieved, the frictional engagement between the members 12 and 18 should be such that the adjusted size of the portions 20 and 22 will be steadfastly maintained. The desired degree of tightness and slidability between the members 12 and 18 as explained above may be achieved by any suitable means.

Figure 4:
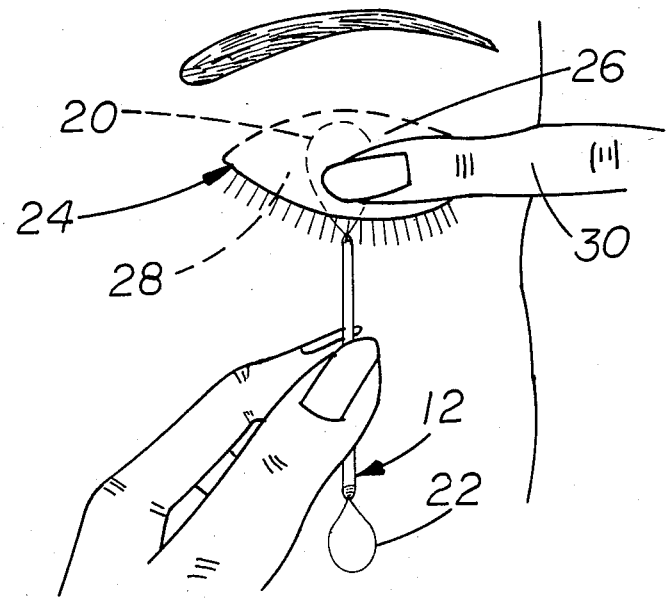

FIGS. 3 and 4 illustrate a typical use of the instrument 10. Once an end portion 20 or 22 of the thread-like member 18 is properly adjusted for the affected eye such as the eye 24, a user simply takes hold of the body member 12 with one hand while raising the eyelid 26 with the other hand as shown in FIG. 3. The adjusted end portion of the member 18 such as the end portion 20 is thereafter inserted against the eye between the eyeball surface 28 and the underside portion of the eyelid 26 such that the loop portion 20 encircles the area on the eye surface where the foreign substance to be removed is located. When the loop portion 20 is properly positioned, the eyelid 26 is closed and a slight pressure is thereafter applied to the upper or lower eyelid 26 adjacent the loop portion 20 such as by using one's finger such as the finger 30 shown in FIG. 4. While maintaining this slight pressure against the eyelid 26, the loop portion 20 is pulled across the eye surface 28 with a single, smooth and steady motion and this movement enables the thread-like portion 20 to engage any foreign substance located on the eye surface within the confines thereof and to remove such substance therefrom. This process may be repeated until all foreign debris is completely removed from the affected eye or until such debris is moved along the eye surface to the lower portion thereof where it may be relatively easily removed by wiping it away by use of a handkerchief or other similar means. The application of some pressure to the outer portion of the eyelid 26 ensures engagement between the thread-like portion 20 and the foreign debris and it provides for the removal thereof from the eye surface and from the underside portion of the eyelid in a single process. This is particularly important because many foreign substances which enter the eye often cling to the underside portion of the eyelid making their removal relatively difficult. In fact, all known means for removing foreign particles from the eye surface are performed with the eyelid in the open position and no means whatsoever are provided for removing foreign substances attached to the underside portion of the eyelid as is possible with the present instrument. In addition, none of the prior art devices provide an adjustable instrument for engaging and manipulating on the surface of the eyeball to remove foreign substances therefrom.

FIG. 5 discloses another embodiment 10' of the construction 10 shown in FIGS. 1 and 2 wherein a non-continuous or open ended flexible thread-like member 18' is utilized in place of the continuous member 18. The opposite end portions 17' and 19' of the member 18' are fixedly attached to the body member 12' and a single reach of the intermediate portion thereof extends through the passageway 14' of the member 12' as shown in FIG. 5. The loop portions 20' and 22' of the thread-like member 18' are adjustable by simply manipulating the single intermediate portion of the member 18' longitudinally within the body member 12' in a manner similar to that described with respect to the instrument 10. In all other respects, the construction and operation of the instrument 10' is substantially the same as the instrument 10.

FIG. 6 discloses another embodiment 32 wherein a non-continuous flexible thread-like member 38 is utilized. The instrument 32 includes an elongated body member 34 having an opening or passageway 36 extending therethrough, the construction of the member 34 being substantially the same as the construction of the member 12. A non-continuous or open ended thread-like member 38 of suitable length extends through the passageway 36 of the member 34 and is positioned therein to form a loop portion 40 at one end portion thereof. The opposite end portions 42 and 44 of the thread-like member 38 extend from the opposite end of the member 34 and the body member 34 frictionally engages the reaches of the thread-like member 38 extending therethrough as previously described. The member 38 is of a material similar to that of the members 18 and 18' and the loop portion 40 is adjustable by manipulating or pulling on the opposite end portions 42 and 44. In this regard, the end portions 42 and 44 should extend a sufficient length from the body end portion 37 such that they will not be completely drawn into the body member 34 during adjustment if the size of the loop portion 40 is increased as by placing a sterile member (not shown) in it to pull it out. Once adjusted, the instrument 32 is used in the same manner as previously explained with respect to the instrument 10. The end surface or face 35 of the member 34 should be made smooth as by rounding it for the same reasons as hereinbefore explained.

Figure 7:
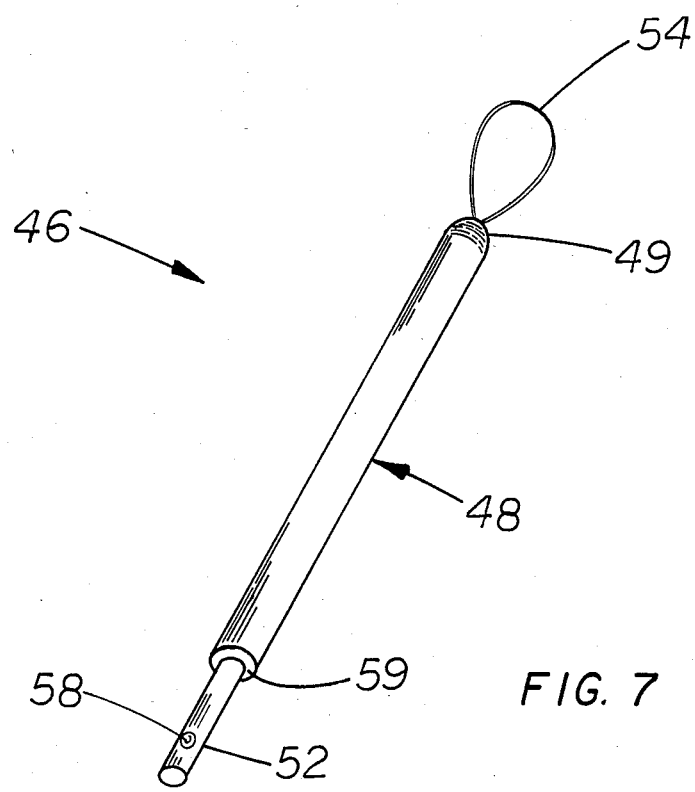
FIG. 7 is a perspective view of still another embodiment of the present instrument.
Figure 8:
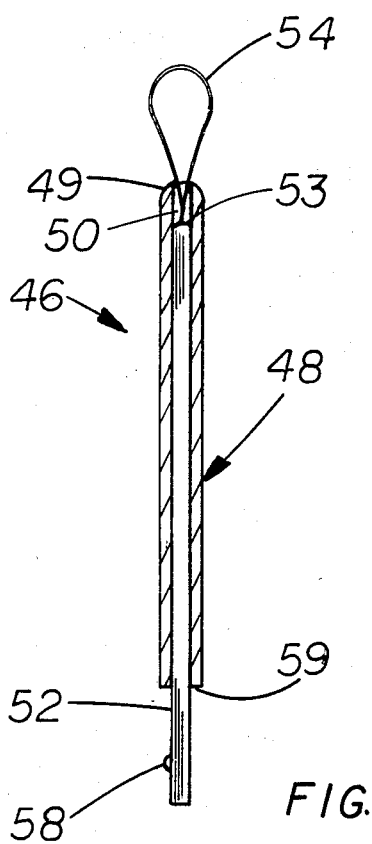
FIG. 8 is an enlarged partial cross-sectional view of the instrument of FIG. 7 showing the loop portion of the thread-like member exposed for use.
Figure 9:
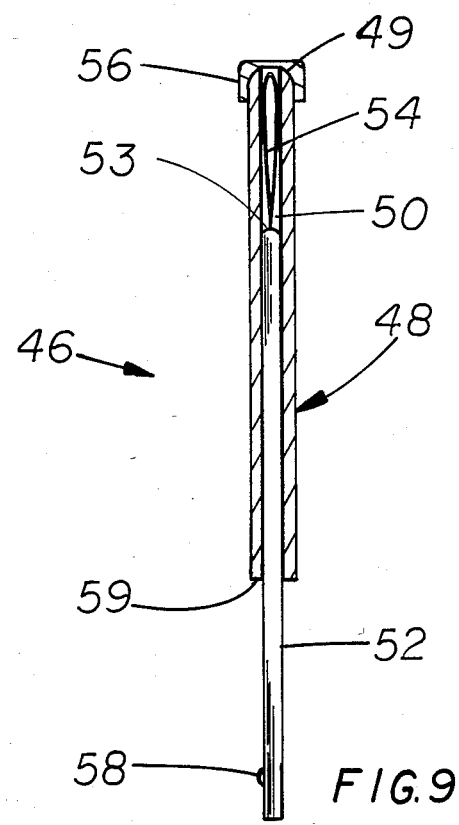
FIG. 9 is an enlarged partial cross-sectional view similar to FIG. 8 showing the loop portion of the thread-like member in a retracted position.

FIGS. 7-9 disclose still another embodiment 46 of the present instrument utilizing still other means for adjusting the size of the loop portion of the flexible thread-like member associated with the instrument. The embodiment 46 includes a first or outer elongated tubular body member 48 having an opening or passageway 50 extending therethrough as best shown in FIGS. 8 and 9. A second or inner elongated body member 52 having a looped flexible thread-like member 54 fixedly attached thereto to extend from one end portion thereof is slidably receivable and movable within the passageway 50 and is of a length such that one end portion thereof may be positioned to extend from and beyond one end portion of the member 48 such as the end portion 59. The flexible thread-like member 54 is made from a suitable sterile material as previously described and the size of the loop member 54 is adjustable by moving the member 52 in the desired direction within the body member 48. When the member 52 is slidably moved in the member 48 toward the end portion 49 thereof or even beyond the end 49, a greater portion of the loop member 54 is exposed thereby increasing the size thereof. In contrast, when the member 52 is pulled rearward in the member 48, it slidably moves away from the end portion 49 and the loop member 54 becomes progressively smaller by being drawn into the passageway 50. This enables a user to adjust the size of the loop portion of the thread-like member 54 without physically touching the member 54 in any way thereby preserving and maintaining the sterility thereof. As previously stated, maintaining the sterility of the flexible member prior to engaging the eye surface is important. The loop portion of the thread-like member 54 may also be drawn totally within the passageway 50 to further ensure sterility prior to use as shown in FIG. 9. In addition, an optional closure member such as the closure member 56 (FIG. 9) may be positioned over the end portion 49 of the body member 48 to maintain sterility of the thread-like member 54 when not in use. The end portion 49 of the member 18 and the end portion 53 of the member 52 are also preferably made smooth by being rounded. The elongated member 52 may also optionally include stop means such as provided by the raised projection 58 which engages the end portion 59 of the member 48 to limit the forward movement of the member 52 in the member 48.

Figure 10:
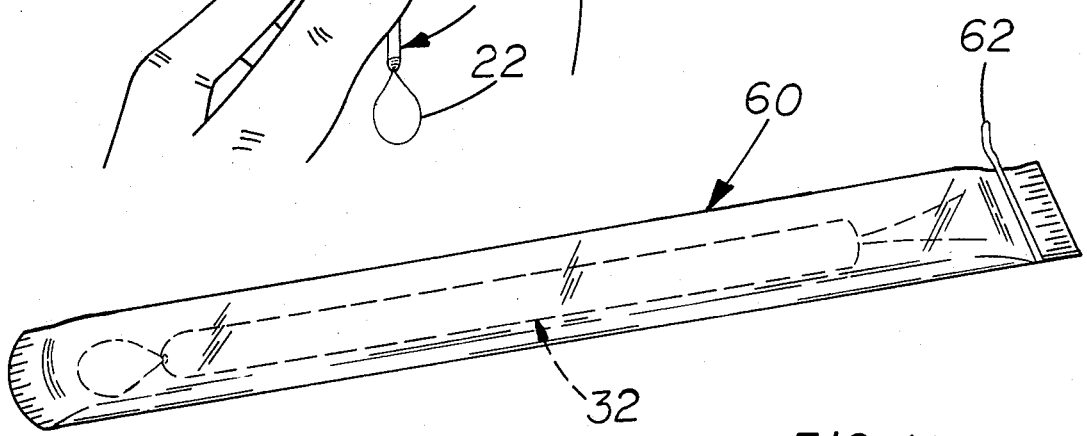
FIG. 10 is a perspective view showing one embodiment of the present instrument wrapped in a sterile prepackaged condition.

Although it is recognized that various materials of construction are available, it is preferred that the body portion of each embodiment of the present instrument such as the members 12, 12', 34, 48 and 52 be constructed of a relatively lightweight durable material such as certain plastic materials which are able to withstand some abuse during normal usage and are readily available and inexpensive. A relatively hard plastic or impact-resistance glass or even metal could likewise be utilized but would increase the cost. It is also anticipated that the present instruments will be individually packaged in a sanitary wrapping somewhat similar to the packaging of a band-aid for use wherever and whenever required. In this regard, FIG. 10 shows a wrapper or package 60 in which one embodiment of the present instrument is positioned at the factory prior to delivery for use. The wrapper includes an elongated container somewhat similar to those used for packaging other articles in a sterilized condition. The wrapper 60 may include a tear strip such as the tear strip 62. The tear strip 62 may be strategically located adjacent to the appropriate end of the present instrument so that when it is pulled to sever the wrapper the instrument can be removed without touching the loop portion of the thread-like member that is to be positioned against the eye surface. Other forms of wrappers and packages can also be used including a package having a tear strip that runs from end to end, a package without a tear strip which is opened simply by tearing off a portion of one end and a tube type package with a cap on one end.

In addition, inasmuch as all embodiments of the present instrument are relatively small and compact, they may be individually sterilized using known techniques and sanitarily packaged, and they may be stored and carried on one's person for use wherever and whenever desired. Additionally, because of their simplicity both structurally and operationally, the present instruments are ideally suited for use by persons of various abilities and ages including use by physicians and hospital personnel. Furthermore, the present instruments are ideally suited for use in first-aid kits, survival kits, medical rescue kits, and other similar medical-type kits. Also, as previously stated, the present instruments can be made to be disposable or they can be constructed for repeated use if desired, and, depending on which is preferred, this may control what type of materials are used in the construction thereof. Where it is anticipated that the various embodiments of the present instrument will be used once and then discarded, the entire instrument can be conveniently constructed from relatively inexpensive materials. If the present instruments are made for repeated use, the flexible thread-like member to be positioned adjacent the eye surface should be resterilized prior to each use thereof. In either case, the various embodiments of the present instrument are all relatively easy to make using known molding and extrusion techniques and known plastics or other substances. The simplicity, durability, and versatility of the various embodiments of the present instrument greatly increases their usefulness and effectiveness as a means for safely and expeditiously removing foreign substances from the eye in a safe and sanitary manner.

Thus there has been shown and described various embodiments of a novel instrument for removing foreign debris from the eye, which instrument fulfills all of the objects and advantages sought therefor. Many changes, modifications, variations and other uses and applications of the present instrument will, however, become apparent to those skilled in the art after considering this specification and the accompanying drawings. All such changes, modifications, variations and other uses and applications which do not depart from the spirit and scope of the invention are deemed to be covered by the invention which is limited only by the claims which follow.

What is claimed is:

1. Means for removing foreign substances from the surface of an eye comprising an elongated member of tubular construction having first and second opposite end portions, a flexible thread-like member, and means including a passageway through said elongated member for cooperatively receiving said thread-like member for slidable movement therein, said thread-like member having one portion thereof extending from the first end portion of said elongated member and another portion thereof extending from the second end portion of said elongated member, each of the extending portions of said thread-like member forming a respective loop element at the first and second end portions of said elongated member, the relative size of one of said loop elements being altered by effecting movement of the other of said loop elements relative to said elongated member, each of said loop elements being adaptable for engaging and manipulating on the surface of the eye to remove foreign substances therefrom.

2. The means defined in claim 1 wherein said elongated member is made of a plastic material.

3. The means defined in claim 1 wherein said flexible thread-like member is made of horse hair.

4. The means defined in claim 1 wherein said flexible thread-like member is made of a surgical suturing material.

5. The means defined in claim 1 wherein said elongated member includes a concave surface portion to facilitate the gripping and manipulating of said member.

6. The means defined in claim 1 wherein said elongated member includes a serrated surface portion to facilitate the gripping and manipulating of said member.

7. The means defined in claim 1 wherein said flexible thread-like member is an endless member.

8. The means defined in claim 1 wherein said flexible thread-like member has opposite first and second ends and an intermediate portion extending therebetween, the intermediate portion of said thread-like member extending through the passageway of said elongated member, the first end of said thread-like member being attached to the first end of said elongated member and the second end thereof being attached to the second end of said elongated member.

9. The means defined in claim 1 wherein the first and second end portions of said elongated member are defined by rounded end surfaces.

* * * * *